(12) United States Patent
Steidler et al.

(10) Patent No.: US 6,605,286 B2
(45) Date of Patent: Aug. 12, 2003

(54) DELIVERY OF BIOLOGICALLY ACTIVE POLYPEPTIDES

(75) Inventors: Lothar Steidler, Ghent (BE); Erik Remaut, Ghent (BE); Jeremy Mark Wells, Cambridge (GB); Richard William Falla Le Page, Cambridge (GB)

(73) Assignees: Vlaams Interuniversitair Instituut voor Biotechnologie, Zwijnaarde (BE); Microbial Technics Limited, Cambridge (GB)

( * ) Notice: Subject to any disclaimer, the term of this patent is extended or adjusted under 35 U.S.C. 154(b) by 0 days.

(21) Appl. No.: 09/060,878

(22) Filed: Apr. 16, 1998

(65) Prior Publication Data

US 2001/0006642 A1 Jul. 5, 2001

Related U.S. Application Data

(63) Continuation of application No. PCT/GB96/02580, filed on Oct. 21, 1996.

(30) Foreign Application Priority Data

Oct. 20, 1995  (GB) .............................................. 9521568

(51) Int. Cl.[7] ........................ A61K 39/00; A61K 39/12; A61K 39/085; A61K 38/00; A01N 37/18
(52) U.S. Cl. ............................. 424/243.1; 424/184.1; 424/192.1; 424/200.1; 424/258.1; 424/199.1; 424/198.1; 435/252.3; 435/320.1; 514/2; 514/3
(58) Field of Search ................... 424/184.1, 243.1, 424/192.1, 200.1, 258.1, 198.1, 199.1; 435/252.3, 320.1; 514/2, 3

(56) References Cited

U.S. PATENT DOCUMENTS

| | | | |
|---|---|---|---|
| 5,032,510 A | * 7/1991 | Kovacevic et al. | 435/69.1 |
| 5,149,532 A | * 9/1992 | Brunell | 424/89 |
| 5,240,705 A | * 8/1993 | Jacobs | 424/164.1 |
| 5,330,753 A | * 7/1994 | Mekalanos et al. | 424/190.1 |
| 5,364,774 A | * 11/1994 | Muir et al. | |
| 5,401,642 A | * 3/1995 | Fiers et al. | |
| 5,401,658 A | * 3/1995 | Fiers et al. | |
| 5,417,986 A | * 5/1995 | Reid et al. | 424/422 |
| 5,455,034 A | * 10/1995 | Nagaraja et al. | 424/130.1 |
| 5,504,005 A | * 4/1996 | Bloom et al. | 435/253.1 |
| 5,547,664 A | * 8/1996 | Charles et al. | 424/93.2 |
| 5,559,007 A | * 9/1996 | Suri et al. | 435/69.1 |
| 5,591,632 A | * 1/1997 | O'Donnell et al. | 435/252.3 |
| 5,733,540 A | * 3/1998 | Lee | |
| 5,824,538 A | * 10/1998 | Branstrom et al. | |
| 6,100,388 A | * 8/2000 | Casas et al. | 536/23.1 |
| 6,130,082 A | * 10/2000 | Majarian et al. | 424/192.1 |
| 6,190,662 B1 | * 2/2001 | Steidler et al. | 424/184.1 |
| 6,190,669 B1 | * 2/2001 | Noriega et al. | 424/258.1 |
| 6,221,648 B1 | * 4/2001 | Le Page et al. | 435/252.3 |
| 6,261,561 B1 | * 7/2001 | Stewart et al. | 424/184.1 |

FOREIGN PATENT DOCUMENTS

| | | | |
|---|---|---|---|
| EP | 0 176 320 | * | 4/1986 |
| EP | 0 449 770 A2 | * | 10/1991 |
| GB | 2278358 A | | 11/1994 |
| GB | 2278358 | * | 11/1994 |
| WO | WO 90/00594 | * | 1/1990 |
| WO | WO 91/06654 | * | 5/1991 |
| WO | WO 93/17117 | * | 9/1993 |
| WO | WO 95/03418 | * | 2/1995 |
| WO | WO 96/11277 | * | 4/1996 |

OTHER PUBLICATIONS

Bojovic et al Applied and Environ. Microbiol. 57/2: 385–388, 1991.*
Steidler et al, J. Bacteriol. 175/23: 7639–7643, 1993.*
Norton et al, FEMS Microbiol Letters 120: 249–256, 1994.*
Wells et al, Molecular Microbiol. 8/6: 1155–1162, 1993.*
Wells et al, Applied and Environ. Microbiol. 59/11: 3954–3959, 1993.*
Wells et al, Int. Diary Journal, 5: 1071–1079, 1995.*
Edwards et al, Infection and Immunity 60/6: 2514–2521, 1992.*
Iwaki et al, Infection Immunity 58/9: 2929–2934, 1990.*
Brett et al. Eur. J. Immunnol. 23: 1608–1614, 1993.*
Sibakov et al, Applied and Environ. Microbiol 57/2: 341–348, 1991.*
Robinson et al, Nature Biotechnology 15:653–57, 1997.*
Steidler et al. Infection and Immunity 66/7:3183–3189, 1998.*
Holmes et al, Infection and Immunity 66/10: 4633–4639, 1998.*
Norton et al, Vaccine, 15/6–7: 616–619, 1997.*
Norton et al, FEMS Immunol. and Medical Microbiol. 14:167–177, 1996.*
Steidler et al, NATO ASI Series vol. H98 pp 63–79, 1996.*
Wells et al, Antonie van Leeuwenhoek 70:317–330, 1996.*
Heath et al., Vaccine, 7: 427–434 (1992).
Rapoport, Current Opinion in Biotechnology, 1: 21–27 (1990).
Boersma et al., (1995) "Lactobacillus as vectors with intrinsic adjuvanticity for safe live mucosal vaccines", Biochemistry Supplement 19A, p. 255.*
Gasson, (1990) "In vivo genetic systems in lactic acid bacteria", FEMS Microbiol. Rev. 87:43–60.*

(List continued on next page.)

Primary Examiner—Nita Minnifield
(74) Attorney, Agent, or Firm—TraskBritt

(57) ABSTRACT

Biologically active polypeptides and/or antigens are delivered by administering to a subject a non-invasive or non-pathogenic bacterium which expresses one or more antigens or polypeptides. The non-invasive or non-pathogenic bacterium can be included in delivery systems or pharmaceutical formulations.

30 Claims, 4 Drawing Sheets

OTHER PUBLICATIONS

Norton, (1995) "Progress in the Development of *Lactococcus lactis* as a Recombinant Mucosal Vaccine Delivery System", *Folia Microbiol.* 40:225–230.*

Steidler et al., (1995) Secretion of Biologically Active Murine Interleukin–2–by *Lactococcus lactis* subsp. *lactis, Appl. Environ. Microbiol.* 61:1627–1629.*

* cited by examiner

DELIVERY OF BIOLOGICALLY ACTIVE POLYPEPTIDES

This application is a continuation of PCT/EB96/02580 filed Oct. 21, 1996.

BACKGROUND OF THE INVENTION

The present invention relates to the delivery of biologically active polypeptides in vivo. In particular, it relates to use of non-invasive bacteria, generally Gram-positive bacteria such as Lactococcus, in providing biologically active polypeptides in the body, especially at mucosa. In one aspect this relates to provision of an adjuvant effect by means of which an immune response raised to an antigen is enhanced. Nucleic acid constructs and host organism for these applications are also provided.

The limited number of adjuvants approved for use in human vaccines (owing to the toxicity or pathogenicity of the most active agents such as Freund's complete adjuvant) and the discovery during the past 20 or more years of numerous polypeptides involved in the proliferation, differentiation and activation of B cells and T cells has drawn attention to the possibility of using these factors (cytokines) to augment responses to vaccines, and to direct the immune response to a particular vaccine along desired pathways. The need for this approach has become even more apparent as recent immunological discoveries have emphasised that cell-mediated and antibody-mediated immune responses are to a large degree mutually exclusive responses. Whether antibody formation or effector T-cells and macrophages are activated is determined by which particular array of cytokines is elicited by any given antigen, pathogen or vaccine. Most important is the functional activity of the types of helper T cells TH1, or TH2, which are involved in the response to any particular antigen or invading pathogen.

Since protective immunity to a pathogenic agent usually arises as a consequence either of antibody-formation (extracellular pathogens, soluble toxins or intracellular pathogens following their release into tissue fluids from dead, dying or productive cells) or of cell-mediated responses (intracellular pathogens) it is in principle highly advantageous to be able to direct immune responses to a vaccine towards either antibody formation or T-cell and macrophage activation. In order that the protective effects of vaccination should persist for as long as possible it is also important to be able to enhance the amplitude, duration and memory components of the immune response.

For these reasons numerous investigators have focused their attention on the possibility of harnessing one or more of the members of the cytokine network of signalling proteins as vaccine adjuvants. This approach may be even more significant when it is considered that the loss of helper T cells—and hence of their cytokine output—may be associated with the failure of individuals suffering from certain types of inherited or acquired immunodeficiencies to be able to respond to particular vaccines.

Although much attention has been paid to the use of cytokines for these purposes only limited success has been reported in harnessing cytokines as adjuvants. Considerable difficulty has been encountered in administering adjuvant cytokines by methods which would be appropriate for inclusion in a vaccine regimen. This difficulty may be exemplified by reference to studies of the use of IL-2 as an adjuvant.

IL-2 has attracted particular attention as a possible adjuvant because, although its principal source is thought to be T helper 1 cells, its major activities are believed to include involvement in wide ranging aspects of immune responses, such as T-cell proliferation, the synthesis of other cytokines, B-cell growth and immunoglobulin synthesis. Thus IL-2 is a T cell-derived cytokine which was first described as a T cell growth factor. It is now known to stimulate growth and differentiation of T cells, B cells, NK cells, monocytes, macrophages and oligodendrocytes. In general, adjuvant activity on the part of IL-2, which has been reported by many workers, has been found to depend on the use of multiple injections of the cytokine or its incorporation into liposomes or oily emulsions. To avoid this need, other workers have either co-expressed IL-2 with vaccine antigens in recombinant bacterial and viral vectors, or have engineered IL-2:antigen fusion proteins; the latter are claimed to provide marked enhancement of the immunogenicity of the antigenic component of the fusion partner.

Other desirable characteristics of vaccines include the need to be as innocuous as possible, to act effectively following the administration of the smallest possible number of doses, and to be suitable for administration via mucosal surfaces (e.g. orally, intranasally, or intra-vaginally) thus obviating the need for hypodermic needles, and activating local, mucosal immune responses in addition to systemic immune responses. The capacity for continued proliferation of live, attenuated pathogens has resulted in numerous studies of the use of recombinant vaccine strains of viruses and bacteria (such as vaccine strains of pox viruses, or of salmonella and tubercle bacteria) as agents for the delivery of heterologous antigens.

We have previously developed systems for the expression of heterologous antigens in the non-pathogenic, non-colonising, non-invasive food-grade bacterium *Lactococcus lactis* (see UK patent GB-2278358B). We have shown previously that *Lactococcus lactis* is able to produce and secrete biologically active murine IL-2 when cultured in vitro (Steidler et al., *Applied and Environmental Microbiology*, April 1995, Vol. 61, No. 4, pp1627–1629). However, owing to the fact that *Lactococcus lactis* is non-invasive—it is indeed not a commensal bacterium nor otherwise normally associated with the colonisation of mucosal surfaces in animals—it was not obvious that this bacterium could be successfully employed in a vaccination strategy which required the formation of an adjuvant cytokine in vivo. We have previously shown (GB-2278358B) that heterologous antigen can be fully antigenic when accumulated within the cytoplasm of *Lactococcus lactis* (from which it is presumed to leak in vivo as the cells are digested by phagocytic cells).

By the manipulation of the appropriate genetic elements we have provided nucleic acid constructs (here artificial operons—coordinately transcribed multigene units) for co-expression in *Lactococcus lactis* of an antigenic polypeptide (exemplified here using tetanus toxin fragment C—TTFC) and a biologically active is cytokine polypeptide (exemplified here using Interleukin 2 and also Interleukin-6).

The IL-6 cytokine has been shown by other workers to have the capacity to augment murine antigen-specific antibody responses in vivo and in vitro, and we have also been able to prepare expression units for IL-6 in *L. lactis*. IL-6 is a multi-functional cytokine secreted by both lymphoid and non-lymphoid cells which is known to possess pleiotropic activities that play a central role in host defence. IL-6 can exert growth-inducing, growth-inhibitory and differentiation-inducing activities, depending on the target cells. These activities include differentiation and/or activation of T cells and macrophages, growth promotion of B cells (seen as growth—promotion of B cell tumour lines in vitro), terminal differentiation (secretion of immunoglobulins) in B cells, and—acting systemically—elicitation of the hepatic acute-phase protein response. Most importantly for the purposes of mucosal immunisation IL-6 has been shown to induce high rate IgA secretion in IgA-committed B cells.

To exemplify the present invention, operons for IL-2 and IL-6 co-expression were separately constructed in a constitutive expression vector (pTREX1, also known as pEX1) so that the transcription of the TTFC gene and the interleukin gene could be controlled by the activity of a lactococcal promoter element of previously defined activity (so-called P1). The constructs were prepared so that, following translation of the mRNA transcribed from the artificial operons, the TTFC antigen would accumulate intracellularly.

When preparations of these bacteria were administered intranasally to mice bacteria engineered to express either Interleukin-2 or Interleukin-6 elicited approximately 10× more anti-TTFC antibody than the constructs which expressed the TTFC alone. Thus, either of these interleukins possessed distinctive adjuvant activity in the experimental system.

It was not obvious from either the capacity of *Lactococcus lactis* to deliver a heterologous antigen or its ability to produce IL-2 in vitro that it would be an appropriate vehicle for a delivery of a cytokine in vivo such that sufficient, active cytokine would be provided to provide an adjuvant effect. *Lactococcus lactis* is non-invasive and non-colonising, which means that when these bacteria are used to deliver an antigen to the immune system, e.g. via a mucosal surface, they are most likely to enter lymphoid tissue as a consequence of phagocytosis by the M (or microfold) cells which sample the contents of mucosal secretions adjacent to mucosal lymphoid tissue. Microparticulate antigens (e.g. tetanus toxoid incorporated into poly L-lactide microparticles) enter lymphoid tissue passively in this way, whereas pathogenic bacteria (or attenuated vaccines) such as species of Listeria, Salmonella and Shigella are able to invade cells and tissues by actively stimulating their uptake into mucosal epithelial cells, in addition to gaining entry via M cells. Since the activity of cytokines as adjuvants has been found previously to require multiple injections or sustained release delivery (Heath and Playfair (1992) *Vaccine* 7: 427–434), and since the cytokines will only be protected from proteolytic digestion within phagocytic cells while the *Lactococcus lactis* cells remain intact or viable, it is unexpected that lactococcal cells expressing cytokines should display marked adjuvant activity as demonstrated herein. This can perhaps be appreciated if it is understood that death and dissolution of the bacterial particles will favour antigen release, but prevent more than very transient production of cytokines. Nevertheless, our findings indicate that the expression of IL-2 or IL-6 by *Lactococcus lactis* does have a marked adjuvant effect. Even if the expresser bacteria were to be administered by a parenteral rather than a mucosal route the same considerations would apply.

Thus, since *Lactococcus lactis* is not invasive—indeed it is not a commensal bacterium and it also depends for its nutrition on the provision of amino acids and peptides which are unlikely to be available in vivo—the demonstration that the cytokine-secreting strains of *L. lactis* are nevertheless able to augment antibody production is surprising. Hence these results demonstrate for the first time that recombinant strains of *Lactococcus lactis* can be used to synthesise and deliver biologically active molecules in vivo. Of particular interest is the fact that these results demonstrate the feasibility of augmenting the mucosal as well as the systemic immune response since IL-6 has been shown to be a cytokine able to induce a high rate of IgA secretion in IgA committed B cells.

The finding that *Lactococcus lactis* is able to sustain its biological activity on a mucous membrane for a sufficient length of time to deliver a biologically active dose of either of two different recombinant cytokines and thereby augment an immune response to a heterologous antigen demonstrates broad applicability for the delivery of polypeptides for purposes other than adjuvant activity alone.

The capacity of *L. lactis* to produce and secrete polypeptides demonstrates that it is possible to utilise these bacteria for in vivo production and delivery of polypeptides which are known to be active at micromolar, nanomolar or picomolar concentrations. Since precise dosing of these polypeptides, and the need for the coincidental introduction of bacterial cells is of lesser concern for veterinary than human applications it is likely that this method for delivering recombinant polypeptides will be especially valuable in veterinary applications. However, even within human medicine, the fact that cytokine output can be constrained to the sites of deposition of harmless bacterial cells, and is available close to the antigen during the earliest phases of the immune response may favour its use in circumstances—such as adjuvant activity—where the biologically active polypeptide is best localised in order to avoid toxic systemic side effects.

SUMMARY OF THE INVENTION

Thus, the present invention provides:
(i) a method of delivering one or more biologically active polypeptides which comprises administering to a subject a non-invasive or non-pathogenic bacterium which expresses said one or more polypeptides;
(ii) A method of delivering one or more antigens which comprises administering to a subject a non-invasive or non-pathogenic bacterium which expresses said one or more antigens; and
(iii) A method of delivering one or more antigens and/or one or more biologically active polypeptides which comprises administering to a subject a non-invasive or non-pathogenic bacterium which expresses both said one or more antigens and said one or more heterologous biologically active polypeptides.

The biologically active polypeptides can be either homologous to the bacterium or heterologous, derived from either eukaryotic sources or prokayotic sources, or their viruses.

According to another aspect of the present invention, there is provided a non-invasive or non-pathogenic bacterium expressing (i) one or more heterologous biologically active polypeptides and (ii) one ore more antigens.

DETAILED DESCRIPTION OF THE INVENTION

"Biological activity" refers to ability to perform a biological function and with reference to a polypeptide implies that the polypeptide adopts a stable conformation ("folded form") which is the same or closely analogous to its native configuration. When folded correctly or substantially correctly, for example with formation of proper folded units, α-helices, β-sheets, domains, disulphide bridges etc., a polypeptide should have the ability to perform its natural function. Generally, the unit of function in a polypeptide is a domain.

Mere ability to be bound by an antibody or other receptor, either with or without elicitation of an immune response, is passive and does not constitute "biological activity". Any antigen has the ability to be bound by an antibody but is not necessarily biologically active.

A "heterologous" polypeptide is one not native to the bacterium, i.e. not expressed by the bacterium in nature or prior to introduction into the bacterium, or an ancestor thereof, of encoding nucleic acid for the polypeptide.

A bacterium according to the present invention will in general be Gram-positive, and may in principle be any innocuous bacterium, for example *Listeria innocua, Staphylococcus xylosus* or a Lactococcus. Lactococci, in particular *Lactococcus lactis,* represent a preferred embodiment of the present invention. Such bacteria are non-colonising.

The skilled person will appreciate that the methods of the present invention could be used to deliver a range of biologically active polypeptides. Examples of suitable polypeptides include ones which are capable of functioning locally or systemically, eg is a polypeptide capable of exerting endocrine activities affecting local or whole-body metabolism and/or the biologically active polypeptide(s) is/are one(s) which is/are capable of the regulation of the activities of cells belonging to the immunohaemopoeitic system and/or the one or more biologically active polypeptides is/are one(s) which is/are capable of affecting the viability, growth and differentiation of a variety of normal or neoplastic cells in the body or affecting the immune regulation or induction of acute phase inflammatory responses to injury and infection and/or the one or more biologically active polypeptides is/are one(s) which is/are capable of enhancing or inducing resistance to infection of cells and tissues mediated by chemokines acting on their target cell receptors, or the proliferation of epithelial cells or the promotion of wound healing and/or the one or more biologically active polypeptides modulates the expression or production of substances by cells in the body.

Specific examples of such polypeptides include insulin, growth hormone, prolactin, calcitonin, luteinising hormone, parathyroid hormone, somatostatin, thyroid stimulating hormone, vasoactive intestinal polypeptide, a structural group 1 cytokine adopting an antiparallel 4α helical bundle structure such as IL-2, IL-3, IL-4, IL-5, IL-6, IL-7, IL-9, IL-10, IL-11, IL-12, IL-13, GM-CSF, M-CSF, SCF, IFN-γ, EPO, G-CSF, LIF, OSM, CNTF, GH, PRL or IFNα/β, a structural group 2 cytokine which are often cell-surface asociated, form symetric homotrimers and the subunits take up the conformation of β-jelly roll described for certain viral coat proteins such as the TNF family of cytokines, eg TNFα, TNFβ, CD40, CD27 or FAS ligands, the IL-1 family of cytokines, the fibroblast growth factor family, the platelet derived growth factors, transforming growth factor β and nerve growth factors, a structural group 3 cytokine comprising short chain α/β molecules, which are produced as large transmembrane pre-cursor molecules which each contain at least one EGF domain in the extracellular region, eg the epidermal growth factor family of cytokines, the chemokines characterised by their possession of amino acid sequences grouped around conserved cysteine residues (the C—C or C—X—C chemokine subgroups) or the insulin related cytokines, a structural group 4 cytokine which exhibit mosaic structures such as the heregulins or neuregulins composed of different domains, eg EGF, immunoglobulin-like and kringle domains.

Alternatively, the biologically active polypeptide can be a receptor or antagonist for biologically active polypeptides as defined above.

The bacterium expresses the biologically active polypeptide and the antigen from nucleic acid contained within it. The nucleic acid may comprise one or more nucleic acid constructs in which nucleic acid encoding the biologically active polypeptide and nucleic acid encoding the antigen are under control of appropriate regulatory sequences for expression in the bacterium.

Suitable vectors comprising nucleic acid for introduction into bacteria can be chosen or constructed, containing appropriate regulatory sequences, including promoter sequences, terminator fragments, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology,* Second Edition, Ausubel et al. eds., John Wiley & Sons, 1992. The disclosures of Sambrook et al. and Ausubel et al. are incorporated herein by reference.

In a preferred embodiment, the coding sequences for the biologically active polypeptide and the antigen are contained in an operon, i.e. a nucleic acid construct for multi-cistronic expression. In an operon, transcription from the promoter results in a mRNA which comprises more than one coding sequence, each with its own suitably positioned ribosome binding site upstream. Thus, more than one polypeptide can be translated from a single mRNA. Use of an operon enables expression of the biologically active polypeptide and the antigen to be coordinated.

In an alternative embodiment, the coding sequences for the biologically active polypeptide and the antigen are part of the same nucleic acid vector, or separate vectors, and are individually under the regulatory control of separate promoters. The promoters may be the same or different.

A nucleic acid construct or vector comprising a coding sequence for a biologically active polypeptide and a coding sequence for an antigen wherein each coding sequence is under the control of a promoter for expression in a non-invasive bacterium (as disclosed—especially a non-commensal and/or non-colonising bacterium e.g. a Lactococcus), whether as an operon or not, is provided by a further aspect of the present invention.

A promoter employed in accordance with the present invention is preferably expressed constitutively in the bacterium. Use of a constitutive promoter avoids the need to supply an inducer or other regulatory signal for expression to take place. Preferably, the promoter directs expression at a level at which the bacterial host cell remains viable, i.e. retains some metabolic activity, even if growth is not maintained. Advantageously then, such expression may be at a low level. For example, where the expression product accumulates intracellularly, the level of expression may lead to accumulation of the expression product at less than about 10% of cellular protein, preferably about or less than about 5%, for example about 1–3%. The promoter may be homologous to the bacterium employed, i.e. one found in that bacterium in nature. For example, a Lactococcal promoter may be used in a Lactococcus. A preferred promoter for use in *Lactococcus lactis* (or other Lactococcus) is "P1" derived from the chromosome of *Lactococcus lactis* (Waterfield N. R.; Le Page, R. W. F.; Wilson P. W. and Wells J. M., *gene,*

165:9–15, 1995), the sequence of which is shown in the following (SEQ ID NO. 1):
GATTAAGTCA TCTTACCTCT TTTATTAGTT TTTTCT- TATA ATCTAATGAT AACATTTTA TAATTAATCT ATAAACCATA TCCCTCTTG GAATCAAAT TTAT- TATCTA CTCCTTTGTA GATATGTTAT AATACAAGTA TC.

The nucleic acid construct or constructs may comprise a secretory signal sequence. Thus, in a preferred embodiment the nucleic acid encoding the biologically active polypeptide may provide for secretion of the biologically active polypeptide (by appropriately coupling a nucleic acid sequence encoding a single sequence to the nucleic acid sequence encoding the polypeptide). Ability of a bacterium harbouring the nucleic acid to secrete the polypeptide may be tested in vitro in culture conditions which maintain viability of the organism.

Suitable secretory signal sequences include any of those with activity in Gram positive organisms such as Bacillus, Clostridium and Lactobacillus. Such sequences may include the α-amylase secretion leader of *Bacillus amyloliquefaciens* or the secretion leader of the Staphylokinase enzyme secreted by some strains of Staphylococcus, which is known to function in both Gram-positive and Gram-negative hosts (see "Gene Expression Using Bacillus", Rapoport (1990) *Current Opinion in Biotechnology* 1:21–27), or leader sequences from numerous other Bacillus enzymes or S-layer proteins (see pp341–344 of Harwood and Cutting, "Molecular Biological Methods for Bacillus", John Wiley & Co. 1990). For Lactococcus the leader sequence of the protein designated Usp45 may be preferred (SEQ ID NO. 2):

```
ATG AAA AAA AAG ATT ATC TCA GCT ATT TTA ATG TCT ACA
met lys lys lys ile ile ser ala ile leu met ser thr GTG
val ATA CTT TCT GCT GCA GCC CCG TTG TCA GGT GTT TAC GCT
ile leu ser ala ala ala pro ley ser gly val tyr ala
```

However, it may be preferable that the antigen accumulates intracellularly. As discussed, preferably the level of accumulation should allow the bacterium to remain viable, i.e. retain some metabolic activity, and may be less than about 10 of cellular protein, preferably about or less than about 5% of cellular protein.

The antigen may in principle be any peptide or polypeptide to which a receptor of the immune system, such as an antibody, can bind. In a preferred embodiment, the antigen is a bacterial toxoid form of a toxin or an antigenic fragment thereof. For good compatibility of expression in Lactococcus, which has a bias towards A/T usage over G/C in its coding sequences (60% A/T), the antigen may be one whose coding sequence is A/T rich (has a higher A/T content than G/C). For instance, the antigen may be a toxoid (or an antigenic fragment thereof), or another immunogenic component from Clostridium or Pneumococcus or other Streptococcus species. Clostridial coding sequences, for example, often have >70% A/T base pair content, as do genes from the important human malarial parasites belonging to the genus Plasmodium.

For use in enhancing an immune response to the antigen, i.e. antigenic peptide or polypeptide, as discussed herein, the biologically active polypeptide preferably has cytokine activity. Cytokines are discussed in "The Cytokine Facts Book", Callard and Gearing (1994), Academic Press. Preferred polypeptides with cytokine activity are interleukins, including Interleukin-2 (IL-2) and Interleukin 6 (IL-6). Many cytokines contain a disulphide bridge and all are secreted from the cells which naturally produce them. The reducing nature of the cytoplasm of bacterial cells would be expected to prevent formation of disulphide bridges. It would not be obvious that a polypeptide which is naturally secreted, especially on which naturally contains a disulphide bridge, would be biologically active when retained in a bacterial cell.

Thus, in one embodiment, the biologically active polypeptide is one which is secreted from cells which naturally produce it.

The use of a cytokine to enhance an immune response to the antigen in accordance with the present invention is particularly apposite for antigens of low immunogenicity. Furthermore, application of an immunogen to a mucosal membrane generally elicits an IgA response. The ability of a vaccine to elicit a good (protective level) mucosal immune response is a highly desirable feature, since it is now known that sIgA antibodies play a vital role in protecting mucosal surfaces against infection. For example, sIgA which binds to the surface of the cholera bacillus has been shown to be capable of preventing experimental cholera in mice. sIgA which effectively neutralised HIV-1 may play an important role in protecting against infection with this virus, since once the virus has gained access to the body a lifelong infection is established. Methods for the reliable and long-lasting induction of mucosal sIgA responses are therefore much sought after, since the great majority of human viruses and bacterial pathogens initiate infections by colonising mucosal surfaces.

Thus, antigens of low immunogenicity from a parasite against which an enhanced IgA response is beneficial may be employed particularly advantageously in the present invention, for instance the P28 immunogen (glutathione-S-transferase) of *Schistosoma mansoni*.

To generate a bacterium according to the present invention, nucleic acid is introduced into a bacterial host cell. Thus, a further aspect of the present invention provides a method comprising introducing nucleic acid as disclosed into a non-invasive bacterium, preferably a Gram-positive bacterium and most preferably a non-commensal, non-colonising bacterium (such as Lactococcus). The introduction may employ any available technique. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. Growing the cells in culture under conditions for expression of the biologically active polypeptide and the antigen may be employed to verify that the bacteria contain the encoding nucleic acid and are able to produce the encoded material.

In a further aspect, the present invention provides a method of delivering a biologically active dose of a polypeptide in vivo, the method comprising administering to an individual a non-invasive bacterium containing nucleic acid for expression of a biologically active polypeptide heterologous to the bacterium. As discussed supra, preferred bacteria include Lactococci such as *Lactococcus lactis* and a preferred route of administration may be by application to mucosa.

Although, it has previously been shown possible to express in such bacteria a heterologous polypeptide in a biologically active form, this has only ever been done in vitro in culture conditions which are optimised for bacterial viability and growth. In vivo, for instance on the mucosal membrane, the bacteria are in an environment which would not be expected to support their growth or viability. It is thus surprising that such bacteria are able to deliver a polypeptide in a dose (amount) which is sufficient for the biological activity of the polypeptide to result in a detectable biological effect.

In a preferred embodiment, the biologically active polypeptide has cytokine activity and the bacterium may also express an antigen. Interleukins such as IL-2 and IL-6 may advantageously be delivered.

It will be appreciated that the methods of the present invention and the use of a non-invasive or non-pathogenic bacterium as described herein provide a wide range of therapeutic methods which would enable the skilled person manipulate, for instance, the immune response of a subject. Thus, the present invention provides, in various other aspects:

(i) a method of regulating the survival, growth, differentiation, effector functions or susceptibility to infection of cells or tissues which comprises administering to a subject a non-invasive or non-pathogenic bacterium as defined herein;

(ii) a method of boosting an immune response against tumour cells or an infection colonising a mucosal surface or adjacent or distant tissue which comprises administering to a subject a non-invasive or non-pathogenic bacterium as defined herein;

(iii) a method of modulating the type of immune response (antibody versus cell-mediated) against a pathogenic infectious agent which comprises administering to a subject a non-invasive or non-pathogenic bacterium as defined herein;

(iv) a method of modulating the infiltration of normal tissues with inflammatory or tumour cells which comprises administering to a subject a non-invasive or non-pathogenic bacterium as defined herein;

(v) a method of controlling the rate of growth, rate of invasion or survival of tumour cells which comprises administering to a subject a non-invasive or non-pathogenic bacterium as defined herein;

(vi) a method of inducing apoptosis in tumour cells which comprises administering to a subject a non-invasive or non-pathogenic bacterium as defined herein;

(vii) a method of downregulating an immune response which comprises administering to a subject a non-invasive or non-pathogenic bacterium which expresses a biologically active polypeptide; and (viii) a method of treating an allergic autoimmune or other immune dysregulative disease state, which comprises administering to a subject a non-invasive or non-pathogenic bacterium which expresses a biologically active polypeptide.

Alternatively stated, when a cytokine and an antigen are both expressed by a bacterium, an aspect of the present invention provides a method of enhancing an immune response to an antigen, the method comprising administering to an individual a non-invasive bacterium containing nucleic acid for expression of a polypeptide with cytokine activity and an antigen.

Enhancement of an immune response, such as an antibody response, preferably provides a level of immune response which is protective of the individual against subsequent challenge with the antigen in a pathogenic context. For example, if the antigen is a bacterial toxoid or a toxin fragment, the level of an antibody response to administration of a bacterium in accordance with the present invention may subsequently protect the individual against pathogenic consequences of challenge with the bacterial toxin, e.g. upon infection with bacteria which produce the toxin.

Administration of the bacterium by application to a mucosal surface may be advantageous in certain contexts by virtue of generating an enhanced immune response at the mucosal membrane (e.g. IgA response) in addition to a systemic response.

The bacterium may be applied in a nutrient medium, i.e. medium containing a substance or substances which sustain (at least in vitro) metabolic activity in the bacterium. Such substances may sustain viability if not growth of the bacterium. Such substances may include an energy source such as glucose, amino acids and so on.

The individual to which the bacterium is administered may be human or animal, i.e. a non-human mammal. Administration may conveniently be nasal, and may be oral, vaginal or anal. In contexts where mucosal administration is not preferred, the bacterium may be administered by any other suitable means within the capacity of those skilled in the art, e.g. by parental routes (i/v, i/p, s/c, i/m).

In a therapeutic context, i.e. where the biological effect of delivery of the polypeptide to an individual is beneficial to that individual, administration is preferably in a "therapeutically effective amount", this being sufficient to show benefit to a patient. Such benefit may be at least amelioration of at least one symptom. In a prophylactic context, the amount may be sufficient to reduce the deleterious effect on the individual of a subsequent pathogenic challenge, for instance by enhancing the immune response. The actual amount administered, and rate and time-course of administration, will depend on the aim of the administration, e.g. the biological effect sought in view of the nature and severity of the challenge, and is the subject of routine optimisation. Prescription of treatment, including prophylactic vaccination, for example decisions on dosage etc, is within the responsibility of general practitioners and other medical doctors.

A composition comprising bacteria may be administered in accordance with the present invention alone or in combination with other treatments, either simultaneously or sequentially.

The present invention also provides a pharmaceutical composition comprising a bacterium as disclosed. Such a pharmaceutical composition is in one embodiment preferably suitable for application to a mucosal membrane.

Pharmaceutical compositions according to the present invention, and for use in accordance with the present invention, may comprise, in addition to the bacterium, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration. For intravenous, cutaneous or subcutaneous injection, or injection at the site of an affliction, a parenterally acceptable aqueous solution may be employed which is pyrogen-free and has suitable pH, isotonicity and stability. Those of relevant skill in the art are well able to prepare suitable solutions. Preservatives, stabilisers, buffers, antioxidants and/or other additives may be included, as required. As discussed, a pharmaceutical comprising a bacterium S for administration in accordance with the present invention may comprise one or more nutrient substances, e.g. an energy source such as glucose, amino acids and so on.

In another aspect, the present invention provides a method of manufacture of a pharmaceutical comprising formulating bacteria as disclosed with a suitable carrier medium for administration to an individual. In one embodiment, the pharmaceutical is suitable for application to a mucosal membrane of an individual.

The present invention also provides a non-invasive bacterium expressing a heterologous biologically active polypeptide, and possibly also an antigen, for pharmaceutical use, i.e. use in a method of treatment of the human or animal body by surgery or therapy, including prophylaxis ("vaccination"). As disclosed, the bacterium may be Gram-positive, is preferably non-commensal and/or non-colonising and suitable examples include Lactococcus. The method preferably comprises administration to a mucosal membrane of an individual, e.g. to enhance an immune response in the individual.

A further aspect of the invention provides the use of any bacterium as disclosed in the manufacture of a composition, i.e. a pharmaceutical composition or medicament, for administration to an individual. Such administration is preferably to a mucosal membrane of the individual and may be to enhance an immune response in the individual, e.g. to an antigen expressed by the bacterium.

BRIEF DESCRIPTION OF THE DRAWINGS

Embodiments of each aspect of the present invention will be apparent from the disclosure and those skilled in the art will appreciate that modifications may be made. Further aspects and embodiments will be apparent. By way of experimental exemplification and not limitation, use of an embodiment of the present invention in achieving a protective level of immune response to an antigen will now be described in detail with reference to the figures.

EXAMPLES

All documents mentioned herein are incorporated by reference.

Example 1

To acquire the simultaneous expression of TTFC and either mIL2 or mIL6, we have chosen for the construction of operons driving the two cistrons under investigation. We made use of vectors for constitutive expression. In general, we try to flank cistrons with an XbaI site immediately prior to the Shine-Dalgarno (SD) sequence and an SpeI site immediately after the stop codon. In this way, multiple cistrons can be easily exchanged and put in various combinations any desired array, since XbaI and SpeI yield the same sticky ends. We have previously achieved the expression of mIL2 and mIL6 by means of the T7 promoter—T7 gene 10 ribosome binding site, so we chose to use the XbaI site present in the g10 ribosome binding site. For this arrangement we knew the SD sequence was well positioned. We choose to put the TTFC cistron in front of the interleukins.

Construction of Plasmids

Figure 1:
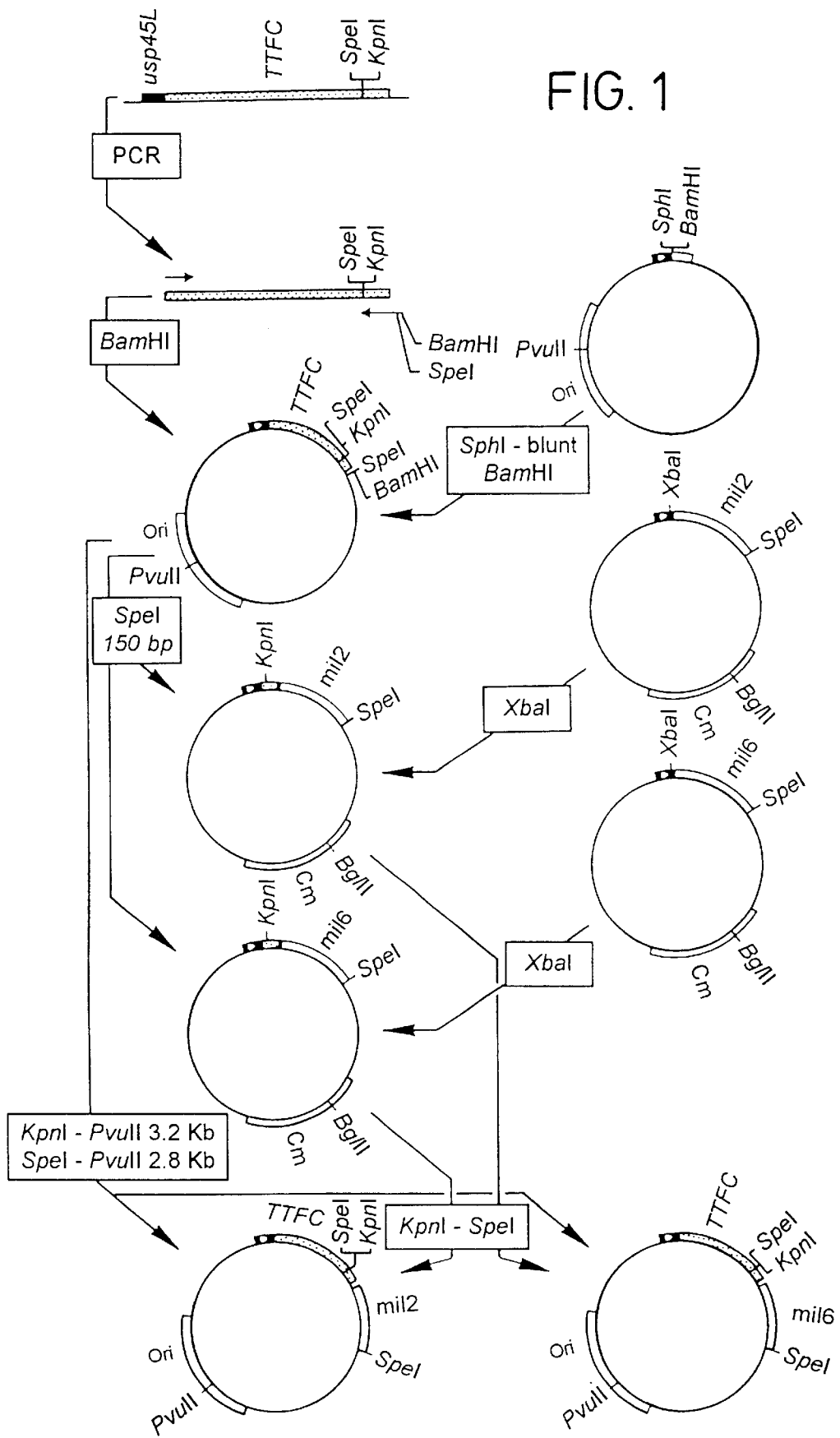
FIG. 1 shows a flow scheme of plasmid constructions. The resulting plasmid pTTI2 may be used to express TTFC and IL-2, and resulting plasmid pTTI6 may be used to express TTFC and IL-6, in an organism such as *Lactococcus lactis*.
Figure 2A:
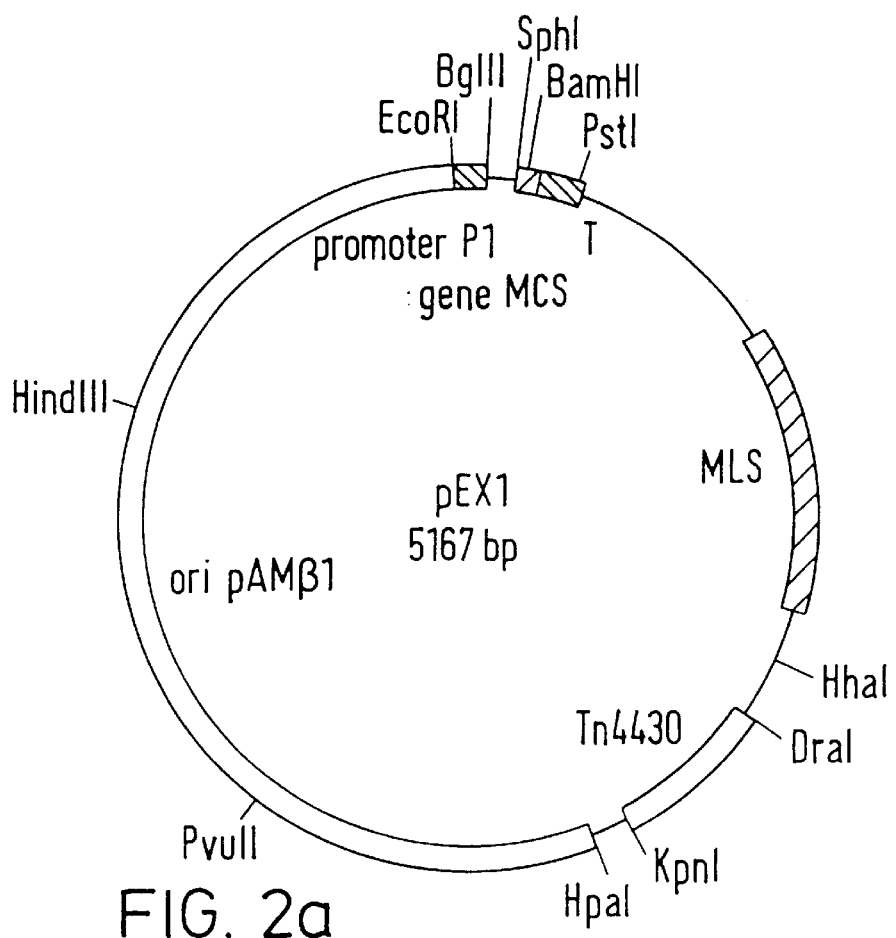
FIG. 2a shows the vector pEX1 (also called pTREX1) into which a gene, such as an operon construct comprising coding sequences for an antigen (e.g. TTFC) and a biologically active polypeptide (e.g. a cytokine such as IL-2 or IL-6), may be inserted at the multiple cloning site (MCS).
Figure 2B:
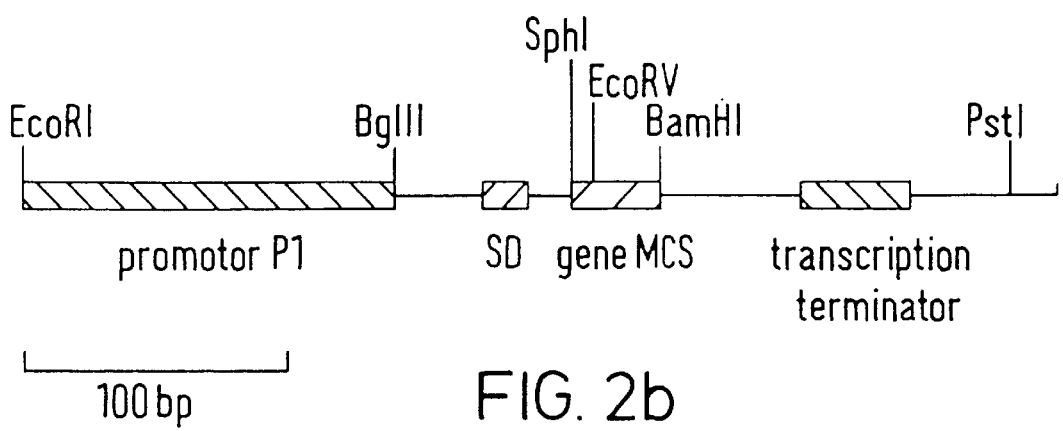
FIG. 2b shows an expanded view of a region of pEX1 (pTREX1) showing the P1 promoter, Shine-Dalgarno sequence (SD) and transcription terminator sequence operably positioned for expression of a gene (including a multi-(di-)cistronic coding sequence) when inserted at the gene MCS (multiple cloning site).
Figure 3:
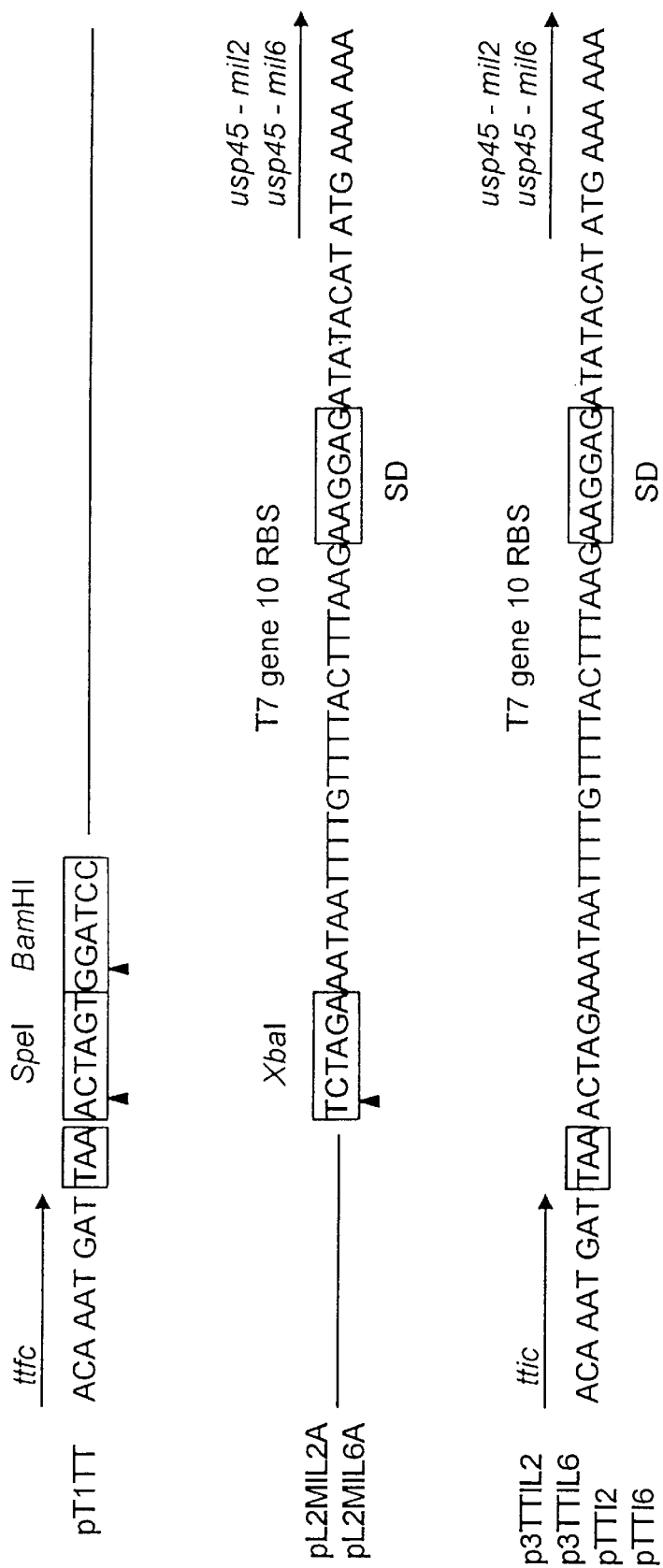
FIG. 3 shows the junction between the TTFC and Interleukin cistrons in the operon employed for expression.

The construction of the plasmids is depicted in FIG. 1. Plasmids carrying mIL2 and mIL6 were subjected to site directed mutagenesis to give extra SpeI sites immediately following the stop codons. The resulting plasmids were called pL2MIL2A and pL2MIL6A, respectively. A plasmid containing a fusion of the USP45 secretion leader and TTFC was used as the template for PCR amplification of the various TTFC sequences needed.

For operons driving intracellular TTFC production, the gene was amplified as a blunt—SpeI/BamHI fragment and cloned in the vector pTREX1, which was cut with SphI, blunted and recut with BamHI. The resulting plasmid was called pT1TT. From this plasmid, the 3' terminal 150 bp, SpeI TTFC fragment was isolated and cloned in the XbaI site of pL2MIL2A and pL2MIL6A. The resulting plasmids were called p3TTIL2 and p3TTIL6. We made use of a KpnI restriction site present in the 3' end of TTFC to reconstruct TTFC, and thus obtain the desired operons, by ligating the KpnI-SpeI fragment from p3TTIL2 and p3TTIL6 with the appropriate KpnI-PvuII and SpeI-PvuII fragments from pT1TT. The resulting plasmids were called pTT12 and pTT16.

Expression of Proteins

The expression of proteins was assayed by antibody detection. For this, colonies of the different strains under investigation were spotted on nitrocellulose membranes, placed on GM17 (difco) solid agar plates containing appropriate antibiotics. The plates were incubated overnight and blocked in PBS containing 2.5% skim milk powder. The filters were revealed with rabbit-anti-TTFC or rabbit anti MIL2. The experiment showed clear TTFC expression in all constructs which hold the TTFC gene. Moreover for pTTI2 and pTTAI2 the coexpression of IL2 and TTFC was detected. Since the junctions between TTFC units and mil6 are identical to those between TTFC and mil2 it may be presumed that IL6 was coexpressed with TTFC equally well.

Preparation of Cells for Immunisations

Bacterial strains for immunisations were grown from fresh overnight cultures which were back diluted at a ratio of 1 ml of overnight culture into 15 ml fresh GM17 medium containing erythromycin at 5 ug/ml and grown at 30° C. Cells were harvested at optical density at 600 nm of between 0.5 and 1.0. Cells were washed in 1/10 of the original culture volume of 0.5% casamino acids, 0.2M sodium bicarbonate, 0.5% glucose before resuspending in 1/200th of the original culture volume and determination of bacterial cell concentration. Cells were then diluted in the above solution to give the required number of cells per immunisation.

Immunisation

Mice were lightly anaesthetised by inhalation using "Metofane". 10 $\mu$l of the bacterial suspension, in a solution of 0.5% casein hydrolysate, 0.2M sodium bicarbonate and 0.5% glucose, were applied to each nostril in turn using an automatic pipette. The animals were observed closely for breathing difficulties until fully recovered from anaesthesia.

Results

Figure 4:
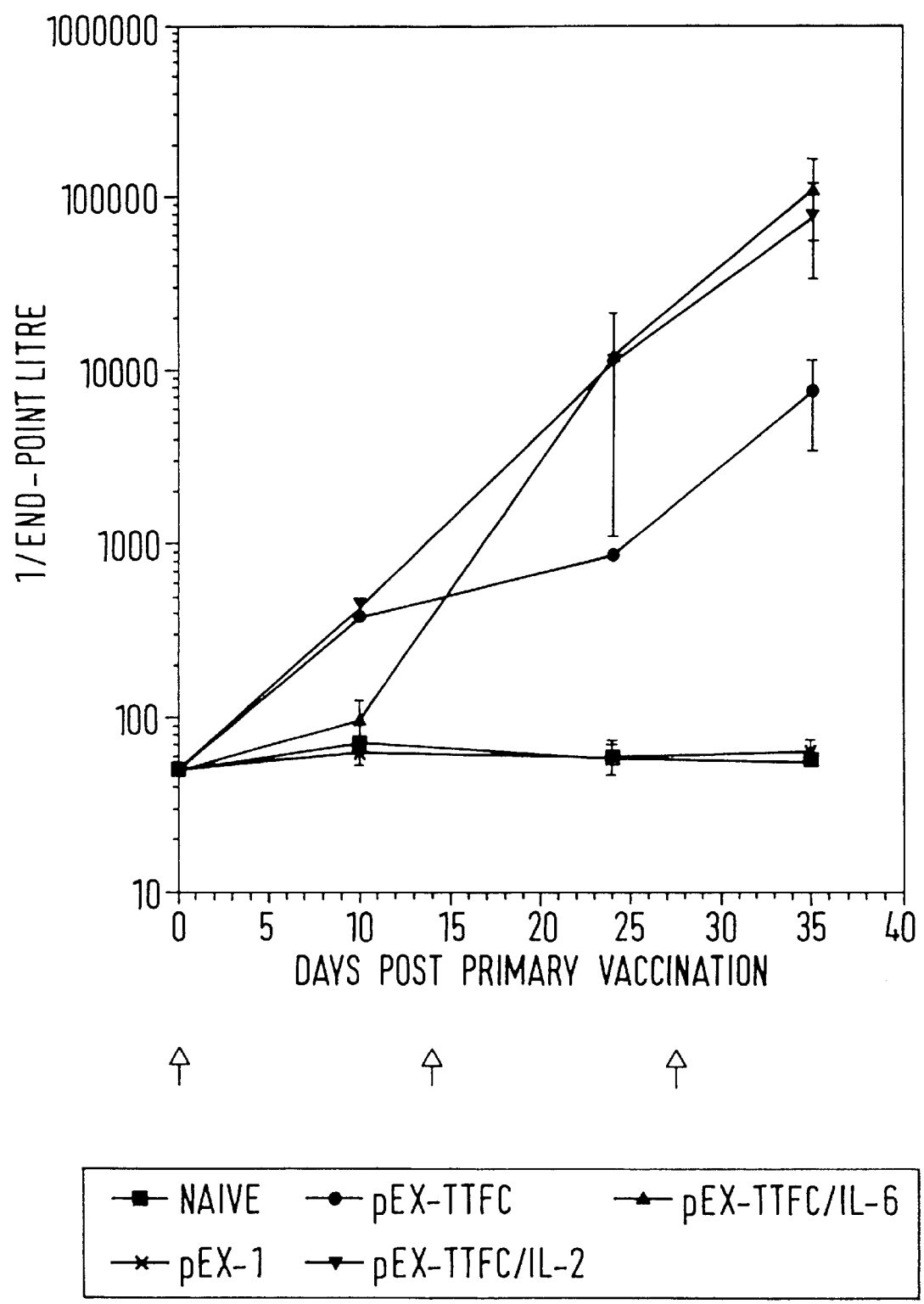
FIG. 4 shows TTFC-specific serum IgG titres of groups of six mice vaccinated intr-nasally with recombinant *Lactococcus lactis* expressing tetanus toxin fragment C (TTFC) with the murine cytokines IL-2 or IL-6.

Results are shown in Table 1 and FIG. 4. Bacteria able to express either Interleukin-2 or Interleukin-6 elicited 10× more anti-TTFC antibody than bacteria expressing TTFC alone.

It is the rule for bacterial toxins that a protective effect is achieved once the antibody titre exceeds a threshold value. The levels of antibody titre found in the mice inoculated with bacteria containing pEX-TTFC/IL-2 and pEX-TTFC/IL-6 far exceeded the threshold value for subsequent protection against tetanus toxin challenge (see FIG. 4, titres at 35 days post vaccination).

Summary of the Experimental Exemplification

Artificial operons for the co-expression of an antigenic polypeptide (tetanus toxin fragment C-TTFC) and biologically active polypeptides (Interleukin 2; Interleukin-6) were separately constructed in a constitutive expression vector (pTREX1) so that the transcription of the TTFC gene and the interleukin gene could be controlled by the activity of a lactococcal promoter element of previously defined activity. The constructs were prepared so that, following translation of the mRNA transcribed from the artificial operons, the TTFC antigen would accumulate intracellularly. A secretion signal sequence was operably linked to the interleukin. When preparations of these bacteria were administered intranasally to mice, bacteria engineered to express either Interleukin-2 or Interleukin-6 elicited approximately 10× more anti-TTFC antibody than the constructs which expressed the TTFC alone. Thus, either of these interleukins possessed distinctive adjuvant activity in the experimental system.

*Lactococcus lactis* is not a commensal bacterium (unlike related species of lactobacilli, which inhabit the crops of chickens and are present in the enteric tracts of many mammals), and also depends for its nutrition on the provision of amino acids and peptides which are unlikely to be available in vivo, so the demonstration that the cytokine-expressing strains of *L. lactis* are nevertheless able to augment antibody production is surprising. These results demonstrate for the first time that recombinant strains of a non-colonising, non-invasive bacterium such as *Lactococcus lactis* can be used to synthesise and deliver biologically active molecules in vivo.

Table 1 (Overleaf)

In the table, "TT/9" is used to indicate inoculation with bacteria expressing TTFC at a dose of $1\times10^9$ bacteria, "TT/8" at a dose of $1\times10^8$ bacteria, and so on. "TT IL-2/9" and "TT IL-6/9" indicate inoculation with bacteria expressing TTFC and IL-2, and TTFC and IL-6, respectively, at a dose of $1\times10^9$ bacteria, "TT IL-2/8" at a dose of 1×10 bacteria and so on. The figures given are ELISA titres for individual mice.

TABLE 1

| IMMUNE RESPONSE DATA - DAY 35 | | | | | |
|---|---|---|---|---|---|
| | End-point titres Bleed 3 Nasal vaccinations data | | | | |
| | TT/9 | TT/8 | TT/7 | TT/6 | |
| | 10000 | 50 | 50 | 50 | |
| | 11000 | 60 | 50 | 50 | |
| | 10000 | 50 | 50 | 75 | |
| | 9000 | 50 | 50 | 50 | |
| | 4500 | 50 | 50 | 70 | |
| | 600 | 110 | 55 | 250 | |
| Mean | 7516.7 | 61.7 | 50.8 | 90.8 | |
| sd | 4089.2 | 24.0 | 2.0 | 78.8 | |
| | TT IL-2/9 | TT IL-2/8 | TT IL-2/7 | TT IL-2/6 | |
| | 14000 | 50 | 50 | 50 | |
| | 30000 | 50 | 50 | 150 | |
| | 100000 | 50 | 50 | 50 | |
| | 100000 | 105 | 150 | 50 | |
| | 120000 | 50 | 80 | 50 | |
| | 100000 | 100 | 50 | 50 | |
| Mean | 77333.0 | 67.5 | 71.7 | 66.7 | |
| sd | 43848.0 | 27.2 | 40.2 | 40.8 | |
| | TT IL-6/9 | TT IL-6/8 | TT IL-6/7 | TT IL-6/6 | |
| | 80000 | 200 | 50 | 50 | |
| | 170000 | 300 | 50 | 50 | |
| | 190000 | 200 | 100 | 50 | |
| | 100000 | 10000 | 50 | 50 | |
| | 50000 | 750 | 50 | 50 | |
| | 80000 | 260 | 400 | 50 | |
| Mean | 111670.0 | 1951.7 | 116.7 | 50.0 | |
| sd | 55648.0 | 3948.3 | 140.2 | 0.0 | |
| | | CONTROLS | | | |
| | pEX 1/9 | pEX 1/8 | pEX 1/7 | pEX 1/6 | Naive |
| | 75 | 75 | 55 | 75 | 60 |
| | 75 | 50 | 75 | 55 | 60 |
| | 50 | 55 | 75 | 75 | 55 |
| | 55 | 50 | 55 | 50 | 55 |
| | 75 | 55 | 75 | 50 | 50 |
| | 60 | 55 | 70 | 50 | 60 |
| Mean | 65.0 | 56.7 | 67.5 | 59.2 | 56.7 |
| sd | 11.4 | 0.9 | 1.0 | 12.4 | 4.1 |

What is claimed is:

1. A method of delivering at least one heterologous biologically active polypeptide to a subject in need of same which comprises administering to the subject a non-invasive or non-pathogenic bacterium which constitutively expresses at least one heterologous biologically active polypeptide to illicit a biological response from the subject.

2. The method of claim 1 wherein the at least one heterologous biologically active polypeptide is an antigen.

3. The method of claim 2 wherein at least one antigen is heterologous to the bacterium.

4. The method of claim 3 wherein the heterologous polypeptide is derived from an eukaryote or its virus, or from a prokaryote or its virus.

5. The method of claim 1 wherein the bacterium is a Gram-positive bacterium.

6. The method of claim 5 wherein the Gram-positive bacterium is *Listeria innocua, Staphylococcus xylosus, Staphylococcus carnosus, Streptococcus gordoni,* a Lactococcus species or a Lactobacillus species.

7. The method of claim 6 wherein the Gram-positive bacterium is *Lactococcus lactis.*

8. The method of claim 5 wherein the bacterium is a non-pathogenic attenuated strain of a Gram-positive pathogenic bacterium.

9. The method of claim 8 wherein the bacterium is *Listeria monocytogenes.*

10. The method of claim 1 wherein the biologically active polypeptide is one which exerts endocrine activities affecting local or systemic metabolism.

11. The method of claim 1 wherein the biologically active polypeptide is one which regulates the activities of cells belonging to the immunohaemopoeitic system.

12. The method of claim 1 wherein the biologically active polypeptide is one which affects the viability, growth and differentiation of normal or neoplastic cells in the body or affecting the immune regulation or induction of acute phase inflammatory responses to injury and infection.

13. The method of claim 1 wherein the biologically active polypeptide is one which enhances or reduces resistance to infection of cells and tissues mediated by chemokines acting on their target cell receptors, or the proliferation of epithelial cells or the promotion of wound healing.

14. The method of claim 1 wherein the biologically active polypeptide is insulin, growth hormone, prolactin, calcitonin, luteinising hormone, parathyroid hormone, somatostatin, thyroid stimulating hormone or vasoactive intestinal polypeptide.

15. The method of claim 1 wherein the biologically active polypeptide is a structural group 1 cytokine adopting an antiparallel 4α helical bundle structure.

16. The method of claim 1 wherein the biologically active polypeptide is a structural group 2 cytokine which forms symmetric homotrimers and the subunits take up the conformation of β-jelly roll described for the TNF family of cytokines, the IL-1 family of cytokines, the fibroblast growth factor family, the platelet derived growth factors, transforming growth factor β or nerve growth factors.

17. The method of claim 1 wherein the biologically active polypeptide is a structural group 3 cytokine comprising short chain α/β molecules, which are produced as transmembrane pre-cursor molecules which each contain at least one EGF domain in the extracellular region.

18. The method of claim 1 wherein the biologically active polypeptide is a structural group 4 cytokine which exhibits mosaic structures.

19. The method of claim 1 wherein the biologically active polypeptide is a receptor or antagonist for a biologically active polypeptide.

20. The method of claim 1 wherein the bacterium expresses an antigen or polypeptide which regulates the survival, growth, differentiation, effector functions or susceptibility to infection of cells or tissues.

21. The method of claim 1 wherein the bacterium expresses an antigen or polypeptide which boosts an immune response against tumour cells or an infection colonising a mucosal surface or adjacent or distant tissue.

22. The method of claim 1 wherein the bacterium expresses an antigen or polypeptide which modulates the type of immune response (antibody versus cell-medicated) against a pathogenic infectious agent.

23. The method of claim 1 wherein the bacterium expresses an antigen or polypeptide which modulates the infiltration of normal tissues with inflammatory or tumour cells.

24. The method of claim 1 wherein the bacterium expresses an antigen or polypeptide which controls the rate of growth, rate of invasion or survival of tumour cells.

25. The method of claim 1 wherein the bacterium expresses an antigen or polypeptide which induces apoptosis in tumour cells.

26. The method of claim 1 wherein the bacterium expresses an antigen or polypeptide which downregulates an immune response.

27. The method of claim 1, wherein the bacterium expresses an antigen or polypeptide which treats an immune dysregulative diseases state.

28. The method of claim 15, wherein the structural group I cytokine is IL-2, IL-3, IL-4, IL-5, IL-6, IL-7, IL-9, IL-10, IL-11, IL-12, IL-13, GM-CSF, M-CSF, SCR, IFN-γ, EPO, G-CSF, LIF, OSM, CNTF, GH, PRL or IFNα/β.

29. The method of claim 28, wherein the structural group I cytokine is IL-2 or IL-6.

30. The method of claim 27, wherein the immune dysregulative diseases is an allergic autoimmune disease state.

* * * * *

UNITED STATES PATENT AND TRADEMARK OFFICE
CERTIFICATE OF CORRECTION

PATENT NO. : 6,605,286 B2
DATED : August 12, 2003
INVENTOR(S) : Lothar Steidler, et al.

It is certified that error appears in the above-identified patent and that said Letters Patent is hereby corrected as shown below:

Column 1,
Line 4, change "PCT/EB96/02580" to -- PCT/GB96/02580 --

Column 4,
Line 55, change "ore" to -- or --

Column 5,
Line 47, change "asociated" to -- associated --

Column 7,
Line 46, change "10" to -- 10% --

Column 14,
Line 7, change "1x10" to -- $1 \times 10^8$ --

Column 17,
Line 17, change "illicit" to -- elicit --

Signed and Sealed this

Twenty-eighth Day of September, 2004

JON W. DUDAS
*Director of the United States Patent and Trademark Office*

SEQUENCE LISTING

```
<160> NUMBER OF SEQ ID NOS: 6

<210> SEQ ID NO 1
<211> LENGTH: 142
<212> TYPE: DNA
<213> ORGANISM: Artificial Sequence
<220> FEATURE:
<223> OTHER INFORMATION: P1 promoter derived from Lactococcus lactis

<400> SEQUENCE: 1
gattaagtca tcttacctct tttattagtt ttttcttata atctaatgat aacattttta     60
```

```
taattaatct ataaaccata tccctctttg gaatcaaaat ttattatcta ctcctttgta      120
gatatgttat aatacaagta tc                                              142
```

<210> SEQ ID NO 2
<211> LENGTH: 81
<212> TYPE: DNA
<213> ORGANISM: Artificial Sequence
<220> FEATURE:
<223> OTHER INFORMATION: Leader Sequence of Usp45 in Lactococcus lactis
<220> FEATURE:
<221> NAME/KEY: CDS
<222> LOCATION: (1)...(81)

<400> SEQUENCE: 2

```
atg aaa aaa aag att atc tca gct att tta atg tct aca gtg ata ctt      48
Met Lys Lys Lys Ile Ile Ser Ala Ile Leu Met Ser Thr Val Ile Leu
  1               5                  10                  15 tct gct gca gcc ccg ttg tca ggt gtt tac gct                           81
Ser Ala Ala Ala Pro Leu Ser Gly Val Tyr Ala
                20                  25
```

<210> SEQ ID NO 3
<211> LENGTH: 27
<212> TYPE: PRT
<213> ORGANISM: Artificial Sequence
<220> FEATURE:
<223> OTHER INFORMATION: Leader Sequence of Usp45 in Lactococcus lactis

<400> SEQUENCE: 3

```
Met Lys Lys Lys Ile Ile Ser Ala Ile Leu Met Ser Thr Val Ile Leu
  1               5                  10                  15

Ser Ala Ala Ala Pro Leu Ser Gly Val Tyr Ala
                20                  25
```

<210> SEQ ID NO 4
<211> LENGTH: 24
<212> TYPE: DNA
<213> ORGANISM: Artificial Sequence
<220> FEATURE:
<223> OTHER INFORMATION: pT1TT in Lactococcus lactis

<400> SEQUENCE: 4

```
acaaatgatt aaactagtgg atcc                                            24
```

<210> SEQ ID NO 5
<211> LENGTH: 51
<212> TYPE: DNA
<213> ORGANISM: Artificial Sequence
<220> FEATURE:
<223> OTHER INFORMATION: pL2MIL2A, pL2MIL6A in Lactococcus lactis

<400> SEQUENCE: 5

```
tctagaaata attttgtttt actttaagaa ggagatatac atatgaaaaa a              51
```

<210> SEQ ID NO 6
<211> LENGTH: 63
<212> TYPE: DNA
<213> ORGANISM: Artificial Sequence
<220> FEATURE:
<223> OTHER INFORMATION: p3TTIL2, p3TTIL6, p3TTI2, pTTI6, in Lactococcus
      lactis -continued

```
<400> SEQUENCE: 6
acaaatgatt aaactagaaa taattttgtt ttactttaag aaggagatat acatatgaaa      60
aaa                                                                   63
```